United States Patent [19]

Toke et al.

[11] Patent Number: 4,739,081

[45] Date of Patent: * Apr. 19, 1988

[54] NEW CROWN ETHER DERIVATIVES, PROCESS FOR THE PREPARATION THEREOF AND ION-SELECTIVE MEMBRANE ELECTROES COMPRISING THE SAME

[75] Inventors: László Toke; Béla Ágai; István Bitter; Erno Pungor; Klára Szepesváry Née Tóth; Erno Lindner; Mária Forró née Horváth; Jeno Havas, all of Budapest, Hungary

[73] Assignee: Magyar Tudomanyos Akademia, Budapest, Hungary

[*] Notice: The portion of the term of this patent subsequent to Jul. 23, 2002 has been disclaimed.

[21] Appl. No.: 667,398

[22] Filed: Nov. 1, 1984

Related U.S. Application Data

[63] Continuation-in-part of Ser. No. 486,285, filed as PCT HU82/00034, Jul. 19, 1982, published as WO 83/00149, Jan. 20, 1983

[30] Foreign Application Priority Data

Jul. 9, 1981 [HU] Hungary ............................ 1999/81

[51] Int. Cl.⁴ ................................. C07D 325/00
[52] U.S. Cl. ............................ 549/351; 549/347
[58] Field of Search ............ 549/347, 351, 352, 348

[56] References Cited

U.S. PATENT DOCUMENTS 4,361,473  11/1982  Young et al. ..................... 549/347
4,554,362  11/1985  Shono et al. ..................... 549/352

FOREIGN PATENT DOCUMENTS 0123386  10/1984  Japan ............................ 549/352
0231083  12/1984  Japan ............................ 549/351

OTHER PUBLICATIONS

Izatt et al. Progress in Macrocyclic Chemistry, vol. 2, (1981), pp. 104-109.

Tamura, H. et al. Bull. Chem. Soc. Japan, vol. 53, (1980), pp. 547-548.
K. Kimura et al., J. Electronanal. Chemistry, vol. 95, (1979), pp. 91-101.

Primary Examiner—Richard L. Raymond
Assistant Examiner—D. L. Dinner
Attorney, Agent, or Firm—Schweitzer & Cornman

[57] ABSTRACT

The invention relates to new crown ether derivatives of the general Formula I

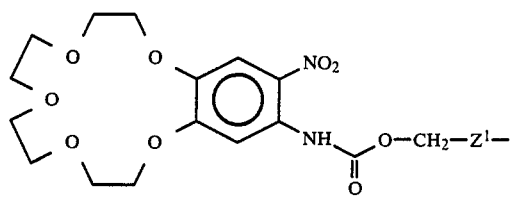

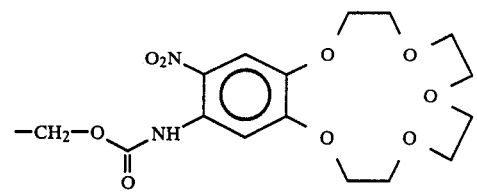

and a process for the preparation thereof wherein $Z^1$ is a group of the general Formula

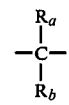

$R_a$ and $R_b$ may be the same or different and $R_a$ represents an alkyl group having 1-4 carbon atoms and $R_b$ is an alkyl group having 1-20 carbon atoms.

The new crown ethers are useful in the preparation of ion-selective electrodes having a long lifetime.

4 Claims, 3 Drawing Sheets

Comparison of potassium ion selective electrodes

Fig. 1

Calibration data of potassium ion selective electrodes

* Philips IS 561-K⁺
** KIMURA,K., MAEDA,T., TAMURA,H., SHONO,T.,
J. Electroanal. Chem., 95 /1979/ 91-101

Fig. 2

Comparison of potassium ion selective electrodes

NEW CROWN ETHER DERIVATIVES, PROCESS FOR THE PREPARATION THEREOF AND ION-SELECTIVE MEMBRANE ELECTROES COMPRISING THE SAME

This application is a continuation-in-part of Ser. No. 486,285, filed as PCT HU82/00034, Jul. 19, 1982, published as WO83/00149, Jan. 20, 1983, now U.S. Pat. No. 4,531,007, issued July 23, 1985.

This invention relates to new crown ether derivatives, process for the preparation thereof and ion-selective membrane electrodes comprising same. More particularly the invention is concerned with new crown ether derivatives useful as cation complexing agent, a process for the preparation thereof and ion-selective membrane electrodes comprising the same.

The new crown ether derivatives of the present invention can be used for cation complex formation under more favourable conditions and provide better results than the known ethers belonging to the state of prior art; the lifetime of membrane sensors comprising the new crown ether derivatives of the present invention used in ion-selective electrodes is longer than that of known membranes and certain analytical characteristic data are better as well.

The invention also relates to ion-selective membrane electrodes comprising a new crown ether derivative of the present invention, the said membranes having a longer lifetime than those prepared from known crown compounds while the performance of the membrane electrodes of the present invention is at least as high as that of the known products.

The present invention is an improvement and further-development of our earlier Hungarian patent application Ser. No. 1999/81 laid open under No. T/26686 without meritorial examination (referred to furtheron as "cited specification").

In the "cited specification" Valinomycin disclosed in Swiss Pat. No. 479,870 is referred to as state of prior art. From the main analytical characteristic features of membrane electrodes prepared by using Valinomycin as active substance selectivity and potential response are generally favourable, however the Rb+ and Cs+ ion-selectivity are not satisfactory for certain fields of application.

The invention protected in the "cited specification" was based on the recognition that if a compound of the general Formula (V)

/V/

(wherein Z is a chemical bond, —CH$_2$—, —(CH$_2$)$_{2-4}$, —CH$_2$OCH$_2$—, —CH$_2$SCH$_2$— or an other cyclic group) is used as ion-selective membrane ligand a high K+ ion-selectivity can be obtained which enables the analytical determination of K+ ion concentration in the presence of other interfering alkaline metal or alkaline earth metal ions (Na+, Ca$^{2+}$, Mg$^{2+}$, Rb+, Cs+). The main analytical features of electrodes prepared by using the said active substances (selectivity, potential response) are equivalent to while the Rb+ and Cs+ ion selectivity surpass that of Valinomycin.

It is known [Kimura et al: J. Electroanal. Chem. 95, 91–101(1979)] that certain compounds belonging to the class of bis-benzo-15-crown-5 derivatives show K+ ion selectivity, however the above compounds disclosed by the authors are not widespreadly used in ion selective electrodes. (Later the authors themselves gave an explanation for this (Microchimica Acta II. 287–296, 1983) by stating that lifetime of the membrane electrode prepared by using these compounds is not satisfactory and the electrodes lose their selectivity after about 200 measurements).

According to our "cited specification" the good ion selectivity of the compounds disclosed therein is due to the fact that although the nitro group attached to the benzene ring of the benzo crown ether decreases the complex stability coefficient of the metal ion (this does not favour selectivity per se) such an intramolecular hydrogen bridge is formed with the adjacent —NH group which forces the two crown ether rings being remote from each other into a favourable stereoconformation and thus the use of the compounds of the general Formula V results in an increase of K+ stability. Thus a K+ ion trap is formed having such internal dimensions which make it capable only for the complexation of K+ ions because the larger ions (Rb+, Cs+) can not get in while the smaller ions (Na+, Li+) fall out. On the other hand the trap forms a "sandwich" with the potassium ion.

Starting from the above discussion of the properties of the crown compounds disclosed in the "cited specification" we were previously of the opinion that the "selectivity does not depend on the quality and length of the chain, connecting the crown ether units".

In order to determine the scope of the fields of application of the invention of the "cited specification" we have carried out various series of experiments. It has been found that the above favourable results can be obtained by using this solution for the determination of the potassium content of natural and industrial waters. On using the electrode according to the "cited specification" for repeated or continuous measurements in biological systems it has been found, however, that the lifetime of the membrane is not satisfactory, presumably due to the slow dissolution of the insufficiently lipophilic ligands. Thus the lifetime of the membrane according to the "cited specification" is unsuitable for use for continuous in vivo measurements e.g. in continuous control of the condition of a patient during surgical operation or in long-lasting automatical series of measurements.

It is the object of the present invention to provide new crown compounds which ensure a longer lifetime for the ion-selective membrane electrode while maintaining the other favourable properties at least on the original level or if possible even improving them.

The present invention is based on the recognition that under maintaining the hydrogen bridge formed according to the "cited specification" the lifetime can be increased and even the K+ ion selectivity can be increased—though to a small extent—by replacing the Z group forming the pole of symmetry of the symmetrical chain linking the two benzo crown ether parts by a group of the general Formula $Z^1$ corresponding to the general Formula (wherein $R_a$ and $R_b$ may be the same or different and $R_a$ represents an alkyl group having 1-4 carbon atoms and $R_b$ is an alkyl group having 1-20 carbon atoms).

The structural difference between the crown ether derivatives of the present invention and those disclosed in the "cited specification" resides merely in the difference between groups Z and $Z^1$, respectively. The effects resulting from this structural modification are however very significant. The following concept has led us to the preparation of the new class of compounds of the present invention.

It would be obvious to eliminate the hydrogen bridge in order to increase lipophility in an advantageous manner. This can not be done, however, because the methylation of the NH moiety of the carbamate group strongly reduces selectivity and the slope of the calibration curve of the electrode prepared from the said N-methyl derivative falls behind that of the theoretical 59.16 mV/decade value.

On replacing group Z by group $Z^1$ in the pole of symmetry of the bridging chain (i.e. in position 2 of the propylene group which constitutes the central part) not only the lifetime is lengthened and the K+ selectivity is improved to a certain extent but the following additional effects and advantages are achieved as well: since the hydrogen bridge is maintained the slope of the calibration curve approaches the therorerical value; practically no "drift" is observed during the measurement; the reproducibility of the measurements improves significantly; the sensitivity to stirring is decreased.

According to a further feature of the present invention there are provided membrane electrodes comprising as active substance a compound of the general Formula I

/I/ wherein $Z^1$ is a group of the general Formula

The compounds of the general Formula I differ from those of the general Formula V by the presence of group $Z^1$ in position 2 of the propylene group in the place of group Z.

The role of common use of the hydrogen bridge and the $Z^1$ group in the achieved advantageous effects is underlined by the fact that if the nitro group is removed the compounds of the general Formula I' thus obtained a strictly related structure possess less significantly selective properties.

/I'/

In order to compare the properties of the compounds of the present invention general Formula VI is referred to

/VI/

(wherein Y is hydrogen or nitro, R is hydrogen or methyl and $Z^2$ stands for Z or $Z^1$) which encompasses the general Formulae I, I' and V.

According to a still further feature of the present invention there is provided a process for the preparation of the new compounds of the general Formula I.

Substituent $R_a$ attached to a carbon atom of group $Z^1$ is preferably methyl, ethyl, n-propyl or n-butyl, particularly methyl, ethyl or n-butyl. Symbol $R_b$ stands preferably for ethyl, n-butyl, n-octyl, n-dodecyl or n-hexadexyl. The chain length of substituent $R_a$ and $R_b$ may be identical or different. If $R_a$ and $R_b$ are of identical chain length they may have the meaning of $R_a$.

The compounds of the general Formula I may be prepared either by total synthesis or by nitrating a crown compound of the general Formula I' containing no nitro group.

According to the total synthesis a crown compound of the Formula II is reacted with a compound of the general Formula III (wherein $Z^1$ is as stated above) in an aprotic solvent.

/II/

$$HO-CH_2-Z^1-CH_2-OH \quad /III/$$

The nitration is carried out by reacting a crown compound of the general Formula I' with nitric acid.

The total synthesis may preferably be carried out by reacting the compounds of the general Formulae II and III in a molar ratio of 2:1 at a temperature of between 0° C. and 50° C. in a chlorinated hydrocarbon or a solvent of the ether type, optionally in the presence of a tertiary amine (e.g. triethyl amine) as catalyst. The product is isolated by removing the solvent and purified by recrystallization from a suitable solvent (e.g. ethyl acetate or methyl isobutyl ketone).

Nitration of a compound of the general Formula I' with nitric acid may preferably be carried out in acetic acid or a chlorinated hydrocarbon as solvent at a temperature ranging from 30° C. to 70° C. The product may be isolated by cooling, filtration or pouring on ice and subsequently by extracting with a chlorinated hydrocarbon. The product may be purified by recrystallization from the above solvent mixture.

The starting material of the Formula II of the total synthesis is disclosed in the "cited specification". The isocyanate may be obtained by reacting an amine of the Formula IV with phosgene in an aromatic solvent having high boiling point in a manner known per se.

/IV/

The compound of the general Formula I or mixtures thereof can be used as active substance of ion-selective electrodes in the following manner:

(a) The selected compound(s) is (are) built into PVC carrier phase in an amount of 0.1-10% of the weight of the membrane by using a suitable plasticizer, preferably a phthalic acid ester, e.g. dipentyl phthalate (DPP), a sebacic acid ester e.g. dioctyl sebacate (DOS) or ortho-nitro-phenyl-octyl ether (ONPOE) or a mixture thereof.

(b) The selected compound(s) is (are) built in an amount of 0.2-10% of the weight of the membrane into a suitable polymer—preferably silicon rubber or PVC, polyamide, polyethylene etc.—which has a dielectrical constant in the range between 2 and 30.

(c) Applying a solution of the selected compound(s) in a suitable solvent (preferably in a plasticizer disclosed in paragraph (a)) onto a porous membrane.

The membranes prepared as described above are installed into a suitable electrode and are connected together with the suitable reference electrode for an analytical instrument.

The correlation between cell voltage and logarithm activity ($-\lg a_{K^+}=pK$) is linear in the range of $pK=1$-$5,0$ and can be characterized by the so called modified Nikolsky equation:

$$EME = E_o + S_{log}\left(a_i + \sum_{i \neq j} K_{ij}^{pot} a_j^{\frac{zi}{zj}}\right) + E_D$$

wherein
EME = cell voltage
$E_o$ = constant reference potential independent of the same solution
$E_D$ = sum of the diffusion potentials in the cell
$a_i$, $a_j$ = activity of the ion to be measured and of the interfering ions
$z_i$, $z_j$ = number of charge of the ion to be measured and of the interfering ions
S = so called Nernst factor, the value of which amounts to 59.16 mV/$z_i$ at 25° C.
$K_{ij}^{pot}$ = selectivity factor Further details of the present invention are to be found in the Examples without limiting the scope of protection to the said Examples.

EXAMPLES

The compounds are referred to with reference to serial numbers. Beside the serial number also the "internal number" of the new compounds of the present invention and the compounds disclosed in the "cited specification" are indicated, the "internal number" comprising a BME sign and a two-figure number (Table 1).

In Table 4 the electrochemical data are summarized for comparative purposes.

In groups A., B. and C. the characteristic data of the ion-selective electrodes prepared from the compounds of the present invention (A), the compounds disclosed in the "cited specification" (B) and the reference material (C) are disclosed.

TABLE 1

| Group | Ser. No. | Internal No. | General Formula VI Y | $Z^2$ | R |
|---|---|---|---|---|---|
| "A" compounds of present invention | 1 | BME-44 | $NO_2$ | $CH_3$<br>\|<br>$-C-$<br>\|<br>$C_{12}H_{25}$ | H |
| | 2 | BME-53 | $NO_2$ | $C_2H_5$<br>\|<br>$-C-$<br>\|<br>$C_2H_5$ | H |

TABLE 1-continued

| Group | Ser. No. | Internal No. | General Formula VI Y | Z² | R |
|---|---|---|---|---|---|
| | 3 | BME-54 | NO₂ | C₄H₉–C(C₄H₉)– | H |
| "B" compound of the "cited specification" | 4 | BME-36 | H | CH₂SCH₂ | H |
| | 5 | BME-15 | NO₂ | CH₂SCH₂ | H |
| | 6 | BME-15-Me | NO₂ | CH₂SCH₂ | CH₃ |
| | 7 | BME-36/2 | H | CH₂CH₂CH₂ | H |
| | 8 | BME-71 | NO₂ | CH₂CH₂CH₂ | H |
| "C" referential compounds | 9 | R$_V$: Valinomycin | | | |
| | 10 | R$_K$: Kimura et al: J. Electroanal. Chem. 95/1979/page 92 III. /n = 3/crown ether derivatives | | | |

The following reference materials are used:
R$_V$=Valinomycin (in a Philips IS 561-K+ electrode)
R$_K$=Crown ether derivatives prepared according to Kimura et al: J. Electroanal. Chem 95 (1979) 91-101.

Preparation of bis crown compounds of the general Formula I (a) Total synthesis

To a solution of 7,08 (20 millimoles) of the isocyanate of the Formula II in 60 ml of anhydrous chloroform 1.32 g (10 millimoles) of 2,2-diethyl-propane-1,3-diol (III);

$$Z^1 = \begin{array}{c} C_2H_5 \\ | \\ -C- \\ | \\ C_2H_5 \end{array}$$

are added. After complete dissolving 2 drops of triethyl amine are added to the solution and the reaction mixture is stirred at room temperature for 2 hours. The solvent is distilled off in vacuo. The yellow solid residue is triturated with ether. The crystalline product is filtered and dried at room temperature. Thus 7.73 (92%) of the crude product 2. are obtained (BME-53, see Table 1). The product is recrystallized from a mixture of ethyl acetate and ether. Thus 5.76 g of the pure product are obtained (68.5%). M.p.: 118°-119° C. The reaction parameters used in the preparation of further compounds of the general Formula I are disclosed in Table 2. The physical, analytical and spectroscopical data of the products are enumerated in Table 3.

(b) Nitration

To a solution of 6,26 g (20 millimole) N-3,4-(1',4',7',10',13'-pentaoxacyclopentadeca-2-ene)-phenyl isocyanate in 60 ml of anhydrous chloroform 1.32 g (10 millimole) of 2,2-diethyl-propane-1,3-diol are added. (III):

$$Z^1 = \begin{array}{c} C_2H_5 \\ | \\ -C- \\ | \\ C_2H_5 \end{array}$$

The reaction mixture is stirred at 50° C. for 5 hours and cooled to 20° C. To the reaction mixture a solution of 3 ml of 65% (specific weight 1.42) nitric acid and 10 ml of glacial acetic acid are added dropwise. The mixture is stirred at room-temperature for a further 10 minutes and at 65° C. for 30 minutes. The reaction mixture is cooled, poured onto crushed ice and the two phases are separated. The aqueous layer is extracted four times with 20 ml of chloroform each. The united organic phases are washed neutral with cold water, dried over magnesium sulfate, filtered and the chloroform solution is evaporated. The residue is purified according to method (a). Yield: 6.23 g (72.5%). Product 2 (BME-53).

In an analoguous manner compounds 1 (BME-44, yield 57%) and 3 (BME-54, yield 61%) are prepared as well.

TABLE 2

Reaction conditions of preparation of bis crown compounds of the general Formula I

| No. | Solvent /catalyst/ | Reaction time/hour/ Temperature/°C./ | Yield % |
|---|---|---|---|
| 1 /BME-44/ | CHCl₃ /—/ | 8 /30/ | 55 |
| | CHCl₃ /TEA/ | 3/30/ | 63 |
| | Dioxan | 1/50/ | 61.5 |
| 2 /BME-53/ | CHCl₃ /—/ | 8/25/ | 64 |
| | CHCl₃ | 3/25/ | 68.5 |
| 3 /BME-54/ | Dioxan /—/ | 6/30/ | 61 |
| | Dioxan /TEA/ | 1/50/ | 66 |

TEA: triethyl amine

TABLE 3

Physical constants of compounds of the general Formula I

| No. | Z¹ | Mp. °C. | Empirical formula /M.w./ | Analysis /%/ calculated | found | IR /KBr/ cm⁻¹ νc = 0 νNH |
|---|---|---|---|---|---|---|
| 1 /BME-44/ | CH₃–C(C₁₂H₂₅)– | 76-77 | C₄₆H₇₀N₄O₁₈ /966/ | C 57.14 H 7.24 N 5.79 | C 57.05 H 7.18 N 5.69 | 1720 3310 |
| 2 /BME-53/ | C₂H₅–C(C₂H₅)– | 117-119 | C₃₇H₅₂N₄O₁₈ 840 | C 52.65 H 6.18 N 6.67 | C 52.48 H 6.11 N 6.60 | 1715 3310 |
| 3 /BME-54/ | C₄H₉–C(C₄H₉)– | 95-96 | C₄₁H₆₀N₄O₁₈ 896 | C 54.91 H 6.69 N 6.25 | C 54.85 H 6.60 N 6.17 | 1720 3310 |

Preparation of a potassium ion-selective membrane by using crown compounds of the general Formula I (1) 30–40, preferably about 34 parts by weight of PVC powder (e.g. SDP Hochmolekular, Lonza AG., Basel, Switzerland) are dissolved in about 2-3 ml. of tetrahydrofuran, and this solution is poured into a vessel containing 0.1-10 parts by weight preferably 2 parts by weight of active ingredient (ionophor) and 65–75, preferably 63,5 parts by weight of a so called plasticizer (an organic solvent of a dielectrical constant of 2–30, and 0–5, preferably 0.5 part by weight of an additive) e.g. (sodium-tetraphenyl-borate or potassium-p-chloro-tetraphenyl-borate).

On a glass plate of flat surface a glass ring of an heigth of 10 mm. and diameter of 25-35 mm. is fixed by means of a rubber ring whereafter 3 ml. of the prepared mixture is poured on the glass ring and covered with a filter paper. Tetrahydrofuran evaporates at room temperature within 1–2 days through the filter paper and at the bottom of the glass ring an elastic membrane of 0.1-0.5 mm. thickness remains as a residue which can be collected readily from the glass plate.

(2) 0.2–10, preferably 2.5 parts by weight of active ingredient and 80–100 mg. preferably 83 parts by weight of dimethyl polysiloxane (e.g. Silopren K 18000, Farbenfabrik Bayer) are dissolved in about 2–4 ml. of carbon tetrachloride. To the solution a cross-linking agent in appropriate amount is added (preferably 14.5 parts by weight). Every catalyst curing cold suitable for cross-linking, such as T-37, (Wacker Chemie GmbH, München) can be used and the mixture is then poured into the glass ring fixed on the glass plate described in 1. and one may further proceed as disclosed in 1.

(3) 0–10, preferably 2.5 parts by weight of active ingredient are pulverized in an achate mortar and dispersed in 80–100 mg. preferably 83 parts by weight of dimethylpolysiloxane (e.g. Silapren K-1000, Farbenfabrik Bayer) until a statistically homogeneous suspension is obtained. Crosslinking agent is added in an amount necessary to curing (e.g. 1 part by weight of dibutyl-Sn-dilaurate and 2 parts by weight of hexaethoxy siloxane) whereafter the mixture is applied to a plastic plate at an equal extent in a thichness of 0.01–1 mm. After curing, what takes at most a few hours, the elastic plate can be collected from the plastic plate.

(4) 0.1–20 parts by weight of active ingredient are dissolved in a water inmmiscible solvent (dielectrical constant of which is 2–30) such as phtalic acid ester, dipentyl phthalate, sebacic acid esters, (dioctyl sebacate), o-nitrophenyl-octyl ether and a mixture thereof, and a porous membrane is wet with the thus obtained solution.

(5) The tetrahydrofuran solution prepared according to 1. containing plasticizer and active ingredient or a carbon tetrachloride dimethylpolysiloxane solution prepared according to 2. containing active ingredient and catalyst or a dimethylpolysiloxane active ingredient suspension prepared according to 3. containing cross-linking agent and/or a catalyst is applied to an electrone-conducting substance, preferably metal silver, silver, silver-chloride wire, platinum or gold fibre, graphit rod etc.

Electrochemical properties of some selected active substances of the general Formula I used as potassium ion-selective membrane electrode A PVC silicon rubber carrier-phase membrane was prepared from the selected active substances (e.g. Nos. 1, 2 or 3) according to Example 1 and 2, whereafter it was built into a suitable electrode body (such as Philips IS-561 Liquid membrane electrode body) and the following measuring cell was formed:

Ag, AgCl | 0.01 M KCl | ion-selective membrane | sample solution ion-selective electrode

| 0.1 M LiOOCCH$_3$ || 0.1 KCl | Ag, AgCl double junction reference electrode EME—lg $a_{K^+}$ calibration curves were plotted in the range of $10^1$—M KCl—$10^{-6}$M KCl using the potential data measured with the above measuring cell. The selectivity factors of the electrodes were determined by the so called separate solution method (Moody, G. J., Thomas, J. D. R.: Selective Ion-Sensitive Electrodes, Watford, Merrow Publishing Co. Ltd., England 1971) by using solutions of concentration of $10^{-1}$M.

Figure 1:
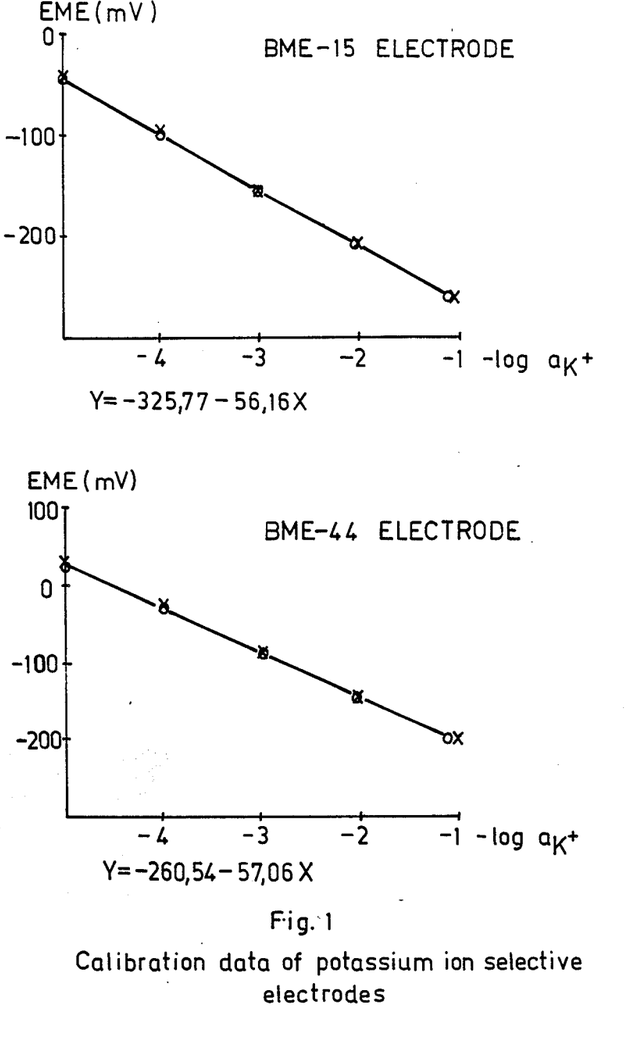
Figure 2:
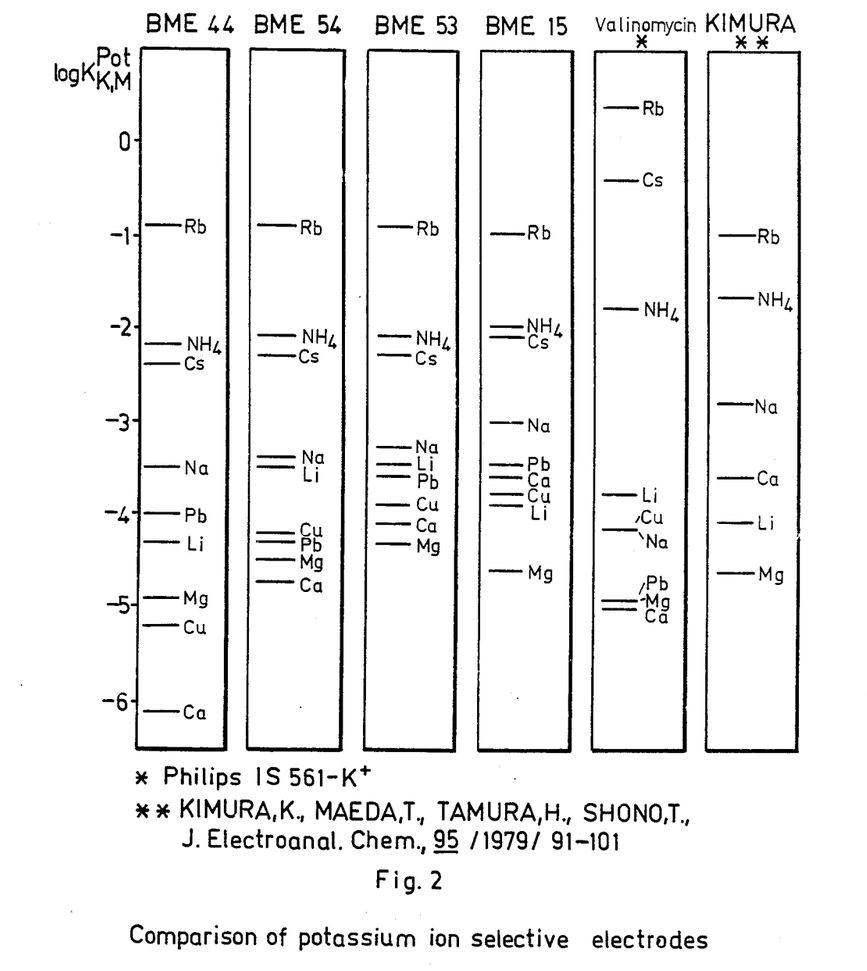

For the sake of more simple comparability the calibration data of the electrode comprising as active substance a compound of the general Formula I (FIG. 1 and Table 4) and the selectivity factors relating to different ions (FIG. 2 and Table 5) are shown together with the corresponding data of electrodes prepared by using the compounds of the present invention and reference compounds. On comparing the calibration and selectivity data of electrodes prepared by using compounds Ser. No. 1, 2 and 3 by means of the same membrane and electrode manufacturing process, respectively, it has been found—contrary to our earlier statements—that the modification of the bridging chain under maintenance of the —NO$_2$ and —NH groups results in a significant increase of K-concentration sensitivity (S~theroetical) and potassium-ion selectivity considerably improves in the presence of sodium-ions ($-\log K_{K,Na}^{pot}=3.5$). This is of particular importance if the potassium content of biological samples is followed or measured, respectively.

Figure 3:
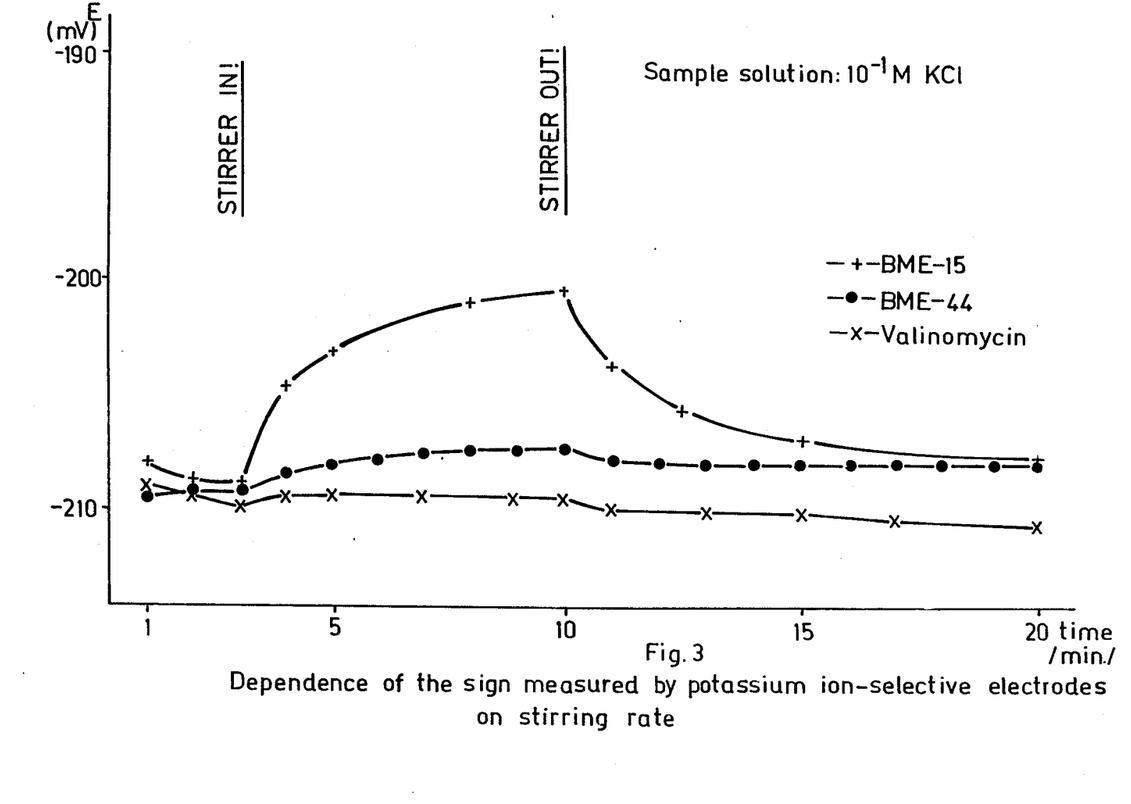

It is of primary importance in use in automatic analysing devices with streaming solutions that the sign measured with the ion-selective electrodes should not at all be dependent on the streaming velocity and stirring rate of the sample solution or should be dependent, but to a small extent, in accordance with theoretical considerations. The dependence of the sign measured by potassium ion-selective electrodes prepared by using BME-15, BME-44 and Valinomycin ligands, respectively, on the rate of stirring is shown on FIG. 3. The values are measured in a potassium chloride solution having a concentration of $10^{-1}$ mole/l by using a laboratory magnetic stirrer. It can be seen from the data of the said Figure that the stirring-sensitivity of the ion-selective electrode comprising BME-44 is much smaller than that of the electrode comprising BME-15 and is approximately the same as that comprising Valinomycin.

From the point of view of the highly accurate measurement of the K$^+$ content of the biological samples a particularly important data is the reproducibility of the potential measurement which amounts to ±0.1 mV in the case of ion-selective electrodes containing BME-44 ligand both in an aqueous potassium chloride solution corresponding to the composition of blood serum and also in blood serum, respectively.

The lifetime of ion-sensitive electrodes is a very important characteristic feature and this parameter is determined by measuring the calibration and sensitivity data of the electrodes at various points of time. Between the measurements the electrodes are stored in a large volume (300-400 ml) of distilled water. It has been found that during a period of one year the potassium concentration sensivity (S value) of electrodes comprising the product BME-44 decreases by 1-2 mV/decade, while the selectivity data change but to an insignificant extent. During this period the $E_o$ value show a standard deviation of but a few mV.

The potassium-ion sensitivity of ion-sensitive electrodes before storage in blood serum and a month after storage, respectively is shown in Table 6. It appears from similar experiments that the ion-sensitive electrode prepared from compound BME-44 is suitable for the determination of $K^+$ ions in blood serum for more than three months.

On comparing the characteristic data of potassium-ion sensitive electrodes prepared by using various ionophores in the same manner it can be stated unambiguously that if the benzo crown ether units are bridged by a branched chain the parameters improve in all cases.

In the specifications the following compounds are used:

Compound 1 (BME-44): 2-n-dodecyl-2-methyl-propylene-1,3-bis-N,N'-[2''-nitro-4'',5''-(1''',4''',7''',10''',13'''-pentaoxa-cyclopentadeca-2'''-ene)-phenyl]-carbamate;

Compound 2 (BME-53): 2,2-diethyl-propylene-1,3-bis-N,N'-[2''-nitro-4'',5''-(1''',4''',7''',10''',13''',-pentaoxa-cyclopentadeca-2'''-ene)-phenyl]-carbamate;

Compound 3 (BME-54): 2,2-di-n-butyl-propylene-1,3-bis-N,N'-[2''-nitro-4'',5''-(1''',4''',7''',10''',13'''-pentaoxa-cyclopentadeca-2'''-ene)-phenyl]-carbamate.

The following abbreviations are used throughout the specification:

ONPOE = o-nitro-phenyl-octylether
NaTPB = sodium tetraphenyl borate
SR = silicon rubber
DPP = dipentyl phthalate
DOS = dioctyl sebacate

TABLE 4

Analytical constants of potassium ion selective electrodes

| No. | Membrane Matrix | Additive | Slope /mV/decade/ | Concentration interval /−log $a_i$/ | Logarithm of selectivity coefficient /log $K_{ij}^{pot}/x$ | | | | | | | | |
|---|---|---|---|---|---|---|---|---|---|---|---|---|---|
| | | | | | j:Na | NH4 | Rb | Cs | Li | Ca | Mg | Cu | Pb |
| 1. /BME-44/ | ONPOE + PVC | — | −56.1 | 1-4 | −3.3 | −2.0 | −0.9 | −2.4 | −4.0 | −5.8 | −4.6 | −5.1 | −3.8 |
| | ONPOE + PVC | — | −55.2 | 1-5 | | | | | | | | | |
| | ONPOE + PVC | NaTPB | −59.3 | 1-4 | | | | | | | | | |
| | | | −57.0 | 1-5 | −3.5 | −2.2 | −0.9 | −2.4 | −4.3 | −6.1 | −4.9 | −5.2 | −4.0 |
| | | | −55.6 | 1-6 | | | | | | | | | |
| | DPP + PVC | — | −58.9 | 1-4 | −3.4 | −2.1 | −0.9 | −2.4 | −3.7 | −5.0 | −4.7 | −4.7 | −4.6 |
| | | | −57.1 | 1-5 | | | | | | | | | |
| | SR | — | −58.2 | 1-4 | −3.4 | −1.9 | — | — | −4.1 | −4.4 | −4.5 | — | — |
| | | | −56.7 | 1-5 | | | | | | | | | |
| 2. /BME-53/ | ONPOE + PVC | — | −55.6 | 1-4 | −3.3 | −2.1 | −0.9 | −2.3 | −3.5 | −4.1 | −4.3 | −3.9 | −3.6 |
| | | | −53.7 | 1-5 | | | | | | | | | |
| 3. /BME-54/ | ONPOE + PVC | — | −55.9 | 1-4 | −3.4 | −2.1 | −0.9 | −2.3 | −3.5 | −4.7 | −4.5 | −4.2 | −4.3 |
| 4. /BME-36/ | ONPOE + PVC | — | −40.4 | 1-4 | −2.2 | −1.5 | — | — | −3.2 | −3.3 | −3.4 | — | — |
| 5. /BME-15/ | ONPOE + PVC | — | −54.0 | 1-5 | −3.2 | −2.0 | −1.0 | −2.1 | −3.9 | −3.6 | −4.6 | −3.8 | −3.5 |
| | ONPOE + PVC | NaTPB | −56.2 | 1-5 | −3.2 | −2.0 | −1.0 | −2.1 | −3.9 | −3.6 | −4.4 | −3.8 | −3.5 |
| | DPP + PVC | — | −57.1 | 1-4 | −3.0 | −2.0 | −1.0 | −2.3 | −3.6 | −4.7 | −4.5 | −3.8 | −3.5 |
| 6. /BME-15-Me/ | ONPOE + PVC | — | −42.3 | 1-4 | −2.2 | −1.4 | — | — | −3.1 | −2.7 | −3.1 | — | — |
| 7. /BME-36/2/ | ONPOE + PVC | — | −50.0 | 1-4 | −1.0 | −0.7 | — | — | −1.5 | −1.2 | −1.8 | — | — |
| 8. /BME-71/ | ONPOE + PVC | — | −54.6 | 1-4 | −2.7 | −1.8 | — | — | — | −3.6 | −4.3 | — | — |
| 9.xx /R$_V$/ | | | −57.8 | 1-5 | −4.2 | −1.8 | +0.4 | +0.4 | −3.8 | −5.0 | −4.9 | −4.2 | −4.9 |
| 10.xxx /R$_K$/ | ONPOE + PVC | | −57.0 | 1-5 | −2.8 | −1.7 | −1.0 | — | — | −4.1 | −3.6 | −4.6 | — | xTo the calculation of the selectivity coefficient theoretical S-value /59,16 mV/decade/ is used
xxPhilips IS 561 K /data measured by us/
xxxdata measured by us

TABLE 5

Selectivity characteristics of potassium ion-selective electrodes

| No. | Interfering cation | log $K_{ij}^{Pot}*$ | | | | | | | | |
|---|---|---|---|---|---|---|---|---|---|---|
| | | j | Na | NH4 | Rb | Cs | Li | Ca | Mg | Cu | Pb |
| 1 /BME-44/ | | | −3.5 | −2.2 | −0.9 | −2.4 | −4.3 | −6.1 | −4.9 | −5.2 | −4.0 |
| 3 /BME-54/ | | | −3.4 | −2.1 | −0.9 | −2.3 | −3.5 | −4.7 | −4.5 | −4.2 | −4.3 |
| 2 /BME-53/ | | | −3.1 | −2.1 | −0.9 | −2.3 | −3.5 | −4.1 | −4.3 | −3.9 | −3.6 |
| 5 /BME-15/ | | | −3.0 | −2.0 | −1.0 | −2.1 | −3.9 | −3.6 | −4.6 | −3.8 | −3.5 |
| 9 /R$_V$/** | | | −4.2 | −1.8 | +0.4 | −0.4 | −3.8 | −5.0 | −4.9 | −4.2 | −4.9 |

TABLE 5-continued

Selectivity characteristics of potassium ion-selective electrodes

| No. | Interfering cation | j | Na | NH₄ | Rb | Cs | Li | Ca | Mg | Cu | Pb |
|---|---|---|---|---|---|---|---|---|---|---|---|
| | | | | | log $K_{ij}^{Pot}$* | | | | | | |
| 10gR*** | | | −2.8 | −1.7 | −1.0 | — | — | −4.1 | −3.6 | −4.6 | — |

*To the calculation of the selectivity coefficient we used the theoretical S /59,16 mV/decade/ value.
**Philips IS 561-K /data measured by us/
***Data measured by us.

TABLE 6

Examination the slope /S/ value of ion-selective electrodes

| No. | | Condition in blood serum*** | |
|---|---|---|---|
| | | before S/$^{mV}$/decade/** | after S/$^{mV}$/decade/** |
| 1 /BME-44/ | a. | 57.5 | 57.9 |
| | b. | 57.2 | 57.0 |
| 2 /BME-53/ | a. | 56.7 | 56.1 |
| | b. | 57.2 | 56.3 |
| 3 /BME-54/ | a. | 56.8 | 57.2 |
| | b. | 57.2 | 57.9 |
| 5 /BME-15/ | a. | 56.5 | 51.5 |

*Composition of electrode membrane:
4 mg ionophor
64 mg PVC
120 mg ONPOE
1 mg NaTPB
**Measured in 10⁻² mol/1–10⁻³ mol /1 KCl solution, comprising 0.1 mol/1 of NaCl
***In the period between the measurements /1 month/ the electrodes were continuosly stored in blood serum /room temperature/.

What we claim is:
1. Crown compounds of the Formula I wherein
$Z^1$ is a group of the general Formula $R_a$ and $R_b$ may be the same or different and $R_a$ represents an alkyl group having 1–4 carbon atoms and $R_b$ is an alkyl group having 1–20 carbon atoms.

2. 2,2-diethyl-propylene-1,3-bis-N,N'-(2''-nitro-4'',5''-1''',4''',7''',10''',13'''-pentaoxacyclopentadeca-2-'''-ene-phenyl)-carbamate.

3. 22-di-n-butyl-propylene-1,3-bis-n,N'-(2''-nitro-4'',5''-1''',4''',7''',10''',13'''-pentaoxacyclopentadeca-2'''-ene-phenyl)-carbamate.

4. 2-n-dodecyl-2-methyl-propylene-1,3-bis-N,N'-(2''-nitro-4'',5''-1''',4''',7''',10''',13'''-pentaoxacyclopentadeca-2'''-ene-phenyl)-carbamate.

* * * * *